US012336929B2

(12) United States Patent
McGregor

(10) Patent No.: US 12,336,929 B2
(45) Date of Patent: Jun. 24, 2025

(54) WARMING BLANKET AND METHOD OF USE THEREOF

(71) Applicant: Solventum Intellectual Properties Company, Maplewood, MN (US)

(72) Inventor: Andrew J. McGregor, West lakeland, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 424 days.

(21) Appl. No.: 17/823,641

(22) Filed: Aug. 31, 2022

(65) Prior Publication Data

US 2023/0096465 A1   Mar. 30, 2023

Related U.S. Application Data

(60) Provisional application No. 63/261,688, filed on Sep. 27, 2021.

(51) Int. Cl.
*A61F 7/00* (2006.01)
*A61F 7/02* (2006.01)

(52) U.S. Cl.
CPC .......... *A61F 7/0097* (2013.01); *A61F 7/0085* (2013.01); *A61F 2007/0091* (2013.01); *A61F 2007/0226* (2013.01)

(58) Field of Classification Search
CPC ........ A61F 2007/006; A61F 2007/0226; A61F 2007/0091; A61F 7/0097
See application file for complete search history.

(56) References Cited

U.S. PATENT DOCUMENTS

| 5,343,579 A | 9/1994 | Dickerhoff et al. |
| 5,716,387 A | 2/1998 | Kappel et al. |
| 5,773,275 A | 6/1998 | Anderson et al. |
| 5,824,025 A * | 10/1998 | Augustine ................. A61F 7/00 607/107 |
| 5,974,605 A | 11/1999 | Dickerhoff et al. |
| 6,156,058 A | 12/2000 | Kappel et al. |
| 6,176,870 B1 | 1/2001 | Augustine |
| 6,241,756 B1 | 6/2001 | Kappel |

(Continued)

FOREIGN PATENT DOCUMENTS

| DE | 20013581 U1 | 2/2001 |
| DE | 10050844 C1 | 3/2002 |

(Continued)

*Primary Examiner* — Tigist S Demie

(57) ABSTRACT

A warming blanket for warming a patient includes a first sheet including a first major surface of the warming blanket, and a second sheet including a second major surface of the warming blanket. The second sheet is sealingly joined to the first sheet to form one or more inflatable portions between the first and second sheets. An adhesive layer is disposed on the first major surface of the first sheet. A liner assembly is disposed on the adhesive layer opposite to the first major surface and fully covers the adhesive layer. The liner assembly includes a plurality of release liners delimited from each other and releasably bonded to the adhesive layer, such that each release liner is independently removable from the liner assembly to expose a corresponding portion of the adhesive layer. Each of the first sheet, the adhesive layer, and the plurality of release liners is air-permeable.

20 Claims, 13 Drawing Sheets

(56) References Cited

U.S. PATENT DOCUMENTS

| | | | |
|---|---|---|---|
| 7,520,889 B2* | 4/2009 | Van Duren | A61F 7/0097 |
| | | | 607/104 |
| 7,819,911 B2 | 10/2010 | Anderson et al. | |
| 8,048,137 B2 | 11/2011 | Pierre et al. | |
| 8,092,895 B2 | 1/2012 | Homölle et al. | |
| 8,172,890 B2 | 5/2012 | Pierre et al. | |
| 2006/0047332 A1 | 3/2006 | Malmberg et al. | |
| 2007/0193588 A1 | 8/2007 | Baumann | |
| 2008/0000006 A1 | 1/2008 | Ochoa et al. | |
| 2008/0203080 A1 | 8/2008 | Fung | |
| 2009/0145542 A1* | 6/2009 | Zoller | B29C 65/5021 |
| | | | 428/41.3 |
| 2009/0228082 A1 | 9/2009 | Ross, III et al. | |
| 2010/0015386 A1 | 1/2010 | Baldauf et al. | |
| 2010/0198320 A1 | 8/2010 | Pierre et al. | |
| 2013/0152950 A1 | 6/2013 | Giap | |
| 2019/0240067 A1* | 8/2019 | Scott | A61F 7/00 |
| 2019/0374377 A1* | 12/2019 | McGregor | A61F 7/0097 |
| 2022/0056310 A1* | 2/2022 | Yamamoto | B32B 27/36 |

FOREIGN PATENT DOCUMENTS

| | | |
|---|---|---|
| EP | 0697201 B1 | 7/1999 |
| EP | 1997942 B1 | 6/2010 |
| EP | 2145555 B1 | 8/2010 |
| EP | 1494733 B1 | 5/2016 |
| EP | 2255759 B1 | 9/2017 |
| WO | 1994005238 A1 | 3/1994 |
| WO | 2009149909 A2 | 12/2009 |

* cited by examiner

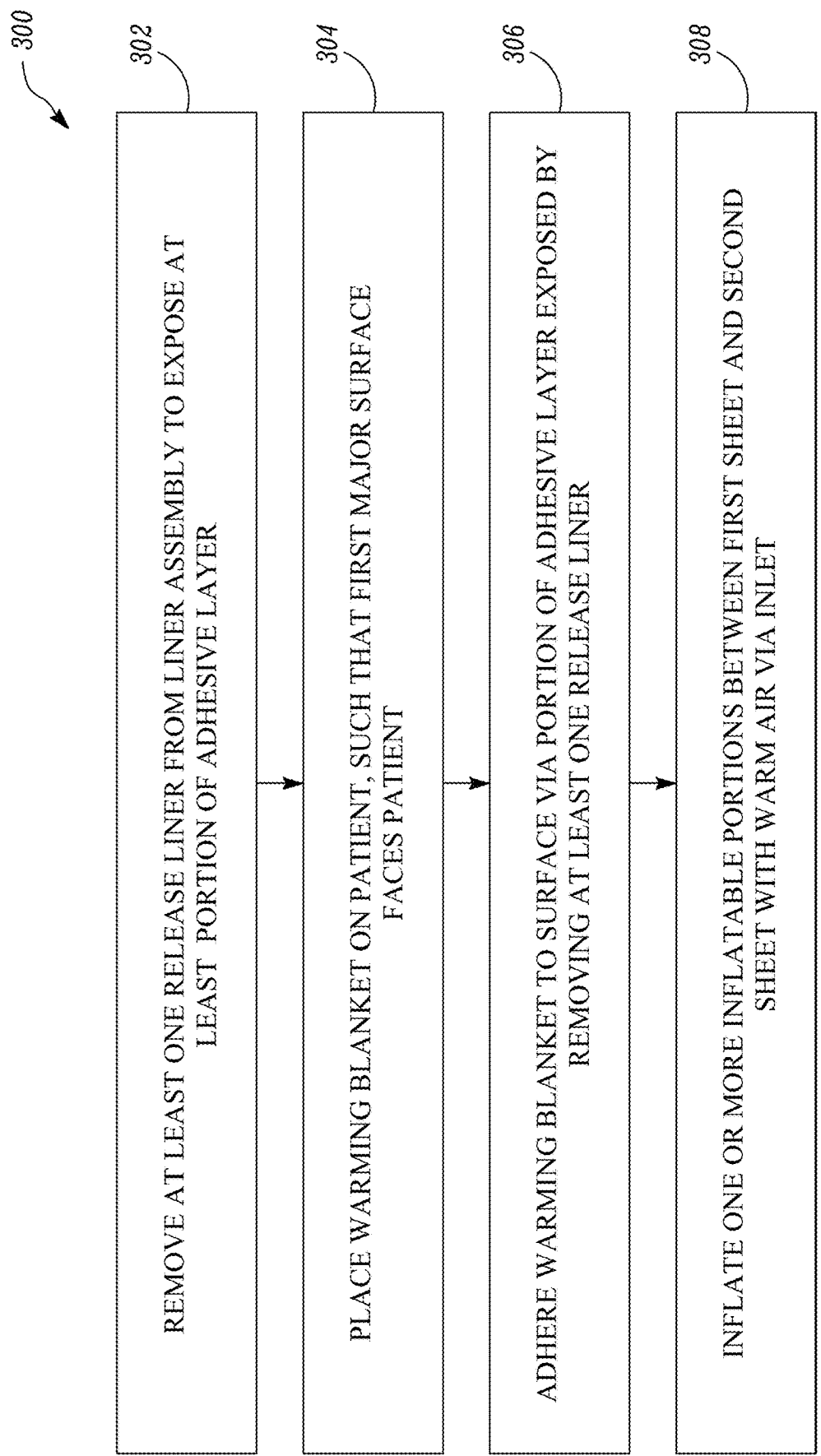

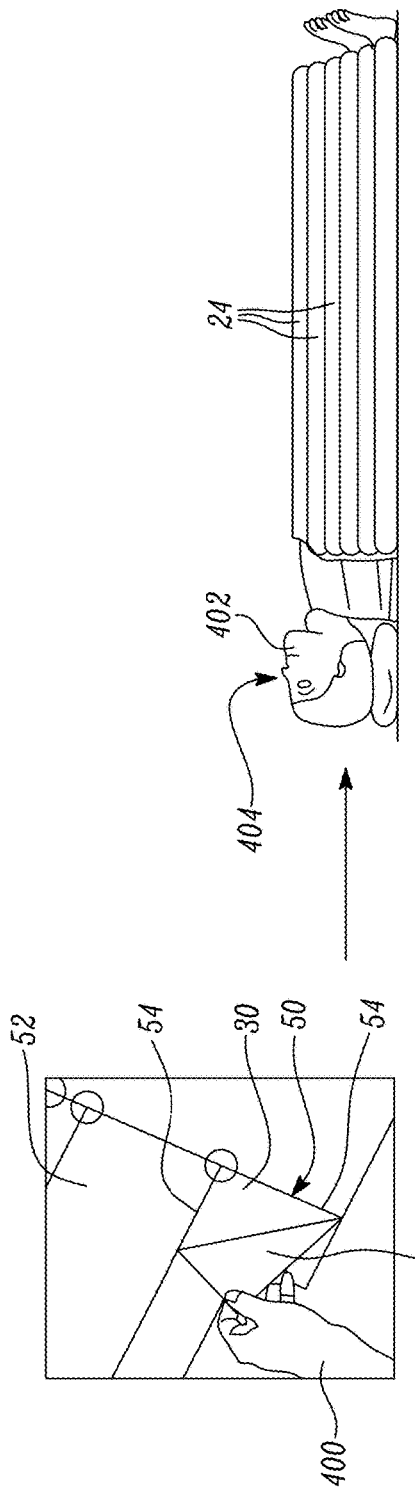
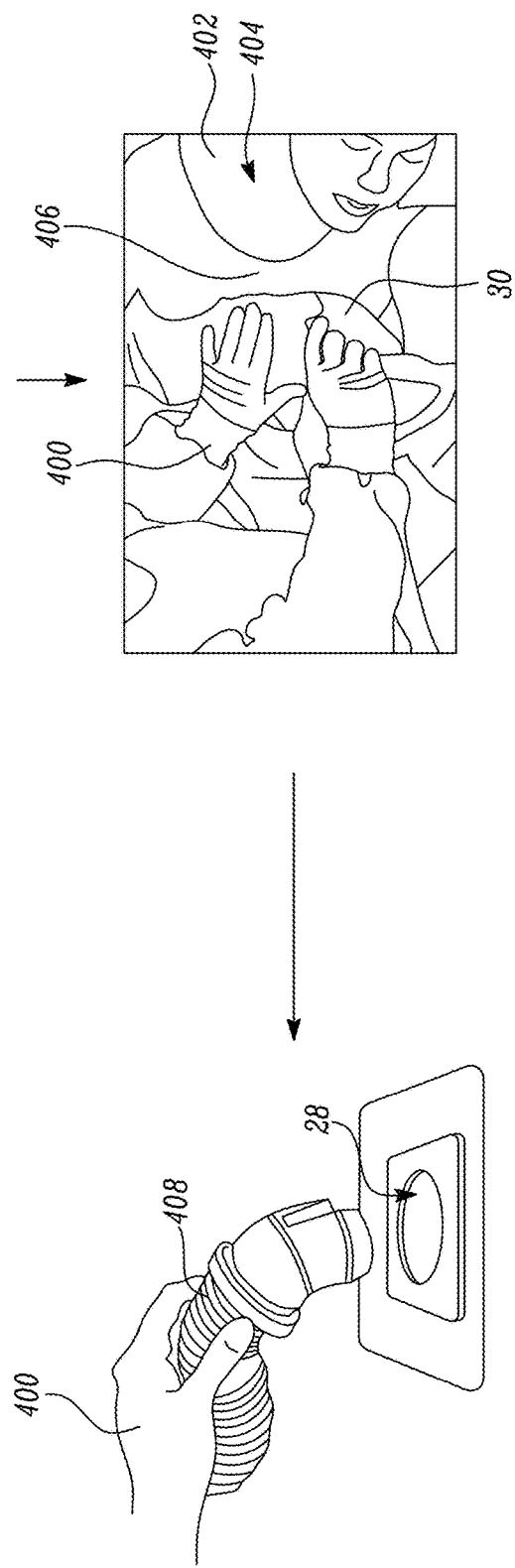

WARMING BLANKET AND METHOD OF USE THEREOF

TECHNICAL FIELD

The present disclosure relates generally to a warming blanket, and in particular to a warming blanket for warming a patient, and a method of using the warming blanket for warming the patient.

BACKGROUND

Convective blankets that transfer heat to a patient are known in the art. For example, convective blankets that receive a stream of a pressurized and warmed air, inflate in response to the pressurized and warm air, distribute the warmed air within a pneumatic structure, and emit the warmed air onto the patient to accomplish objectives such as increasing comfort, reducing shivering, and treating or preventing hypothermia are known in the art.

Conventional convective blankets are generally designed to accommodate a specific position (e.g., a surgical position) of the patient. Consequently, conventional convective blankets with different designs are typically required for different positions of the patient. In some positions of the patient, multiple conventional convective blankets having different designs may be required to effectively accommodate and cover the patient. Further, the conventional convective blankets may provide inadequate securement to the patient during a medical procedure.

SUMMARY

Generally, the present disclosure relates to a warming blanket for warming a patient. The present disclosure further relates to a method of using the warming blanket for warming the patient.

In a first aspect, the present disclosure provides a warming blanket for warming a patient. The warming blanket includes a first sheet including a first major surface of the warming blanket. The warming blanket further includes a second sheet including a second major surface of the warming blanket opposite to the first major surface. The second sheet is sealingly joined to the first sheet to form one or more inflatable portions between the first sheet and the second sheet. The warming blanket further includes an adhesive layer disposed on at least a portion of the first major surface of the first sheet. The adhesive layer includes an adhesive. The warming blanket further includes a liner assembly disposed on the adhesive layer opposite to the first major surface and fully covering the adhesive layer. The liner assembly includes a plurality of release liners delimited from each other and releasably bonded to the adhesive layer, such that each release liner is independently removable from the liner assembly to expose a corresponding portion of the adhesive layer. Each of the first sheet, the adhesive layer, and the plurality of release liners is air-permeable.

In a second aspect, the present disclosure provides a method of using the warming blanket of the first aspect. The method includes removing at least one release liner from the liner assembly to expose at least a portion of the adhesive layer. The method further includes placing the warming blanket on the patient, such that the first major surface faces the patient. The method further includes adhering the warming blanket to a surface via the portion of the adhesive layer exposed by removing the at least one release liner. The method further includes inflating the one or more inflatable portions between the first sheet and the second sheet with warm air via an inlet, such that the warm air fluidly communicates with the patient through the first sheet, the adhesive layer, and at least one of the plurality of release liners.

In a third aspect, the present disclosure provides a warming blanket for warming a patient. The warming blanket includes a first sheet including a first major surface of the warming blanket. The warming blanket further includes a second sheet including a second major surface of the warming blanket opposite to the first major surface. The second sheet is sealingly joined to the first sheet to form one or more inflatable portions between the first sheet and second sheet. The warming blanket further includes an adhesive layer including a plurality of adhesive portions disposed on the first major surface of the first sheet and spaced apart from each other, such that the first major surface of the first sheet includes a plurality of non-adhesive portions alternating with the plurality of adhesive portions. Each adhesive portion includes an adhesive. Each non-adhesive portion is free of the adhesive. The warming blanket further includes a liner assembly disposed on the adhesive layer opposite to the first major surface and fully covering the adhesive layer. The liner assembly includes a plurality of release liners delimited from each other and releasably bonded to the adhesive layer, such that each release liner is independently removable from the liner assembly to expose a corresponding portion of the adhesive layer. Each of the first sheet, the adhesive layer, and the plurality of release liners is air-permeable.

In a fourth aspect, the present disclosure provides a method of using a warming blanket having a first sheet, a second sheet sealingly joined to the first sheet to form one or more inflatable portions between the first sheet and the second sheet, an adhesive layer disposed on at least a portion of a first major surface of the first sheet, and a liner assembly disposed on and fully covering the adhesive layer. The liner assembly has a plurality of release liners. The method includes removing at least one release liner from the liner assembly to expose at least a portion of the adhesive layer. The method further includes placing the warming blanket on a patient, such that the first major surface faces the patient. The method further includes adhering the warming blanket to a surface via the portion of the adhesive layer exposed by removing the at least one release liner. The method further includes inflating the one or more inflatable portions between the first sheet and the second sheet with warm air via an inlet, such that the warm air fluidly communicates with the patient through the first sheet, the adhesive layer, and at least one of the plurality of release liners.

BRIEF DESCRIPTION OF THE DRAWINGS

Exemplary embodiments disclosed herein may be more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labeled with the same number.

FIG. 11 is a flowchart depicting various steps of a method of using a warming blanket according to an embodiment of the present disclosure; and FIGS. 12A-12D are schematic views depicting various steps of using the warming blanket according to an embodiment of the present disclosure.

DETAILED DESCRIPTION

Figure 1:
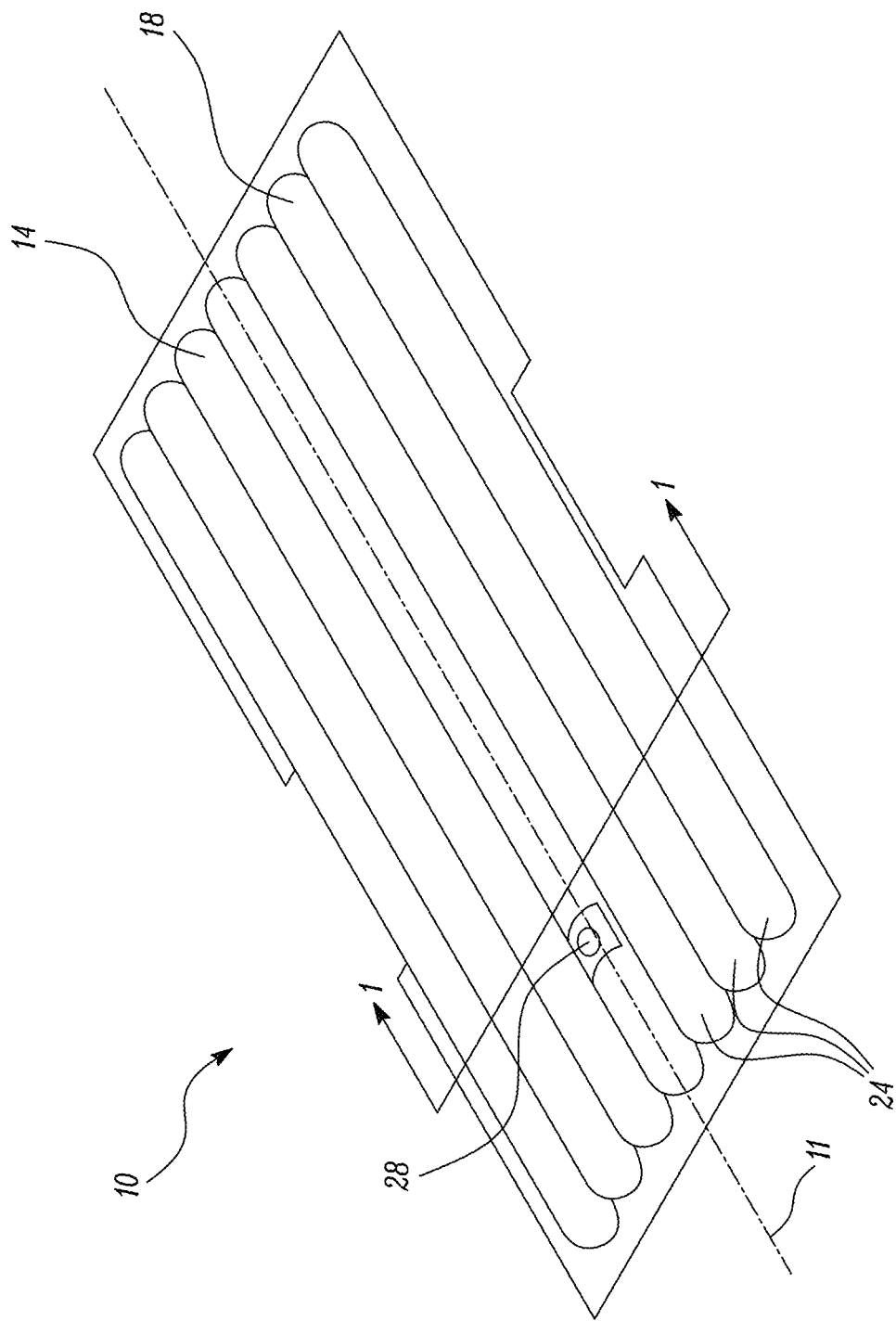
FIG. 1 is a schematic perspective view of a warming blanket for warming a patient according to an embodiment of the present disclosure.

In the following description, reference is made to the accompanying figures that form a part thereof and in which various embodiments are shown by way of illustration. It is to be understood that other embodiments are contemplated and may be made without departing from the scope or spirit of the present disclosure. The following detailed description, therefore, is not to be taken in a limiting sense.

In the following disclosure, the following definitions are adopted.

As recited herein, all numbers should be considered modified by the term "about". As used herein, "a," "an," "the," "at least one," and "one or more" are used interchangeably.

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties).

The term "substantially", unless otherwise specifically defined, means to a high degree of approximation (e.g., within +/−10% for quantifiable properties) but again without requiring absolute precision or a perfect match.

The term "about", unless otherwise specifically defined, means to a high degree of approximation (e.g., within +/−5% for quantifiable properties) but again without requiring absolute precision or a perfect match.

Terms such as same, equal, uniform, constant, strictly, and the like, are understood to be within the usual tolerances or measuring error applicable to the particular circumstance rather than requiring absolute precision or a perfect match.

As used herein, the terms "first" and "second" are used as identifiers. Therefore, such terms should not be construed as limiting of this disclosure. The terms "first" and "second" when used in conjunction with a feature or an element can be interchanged throughout the embodiments of this disclosure.

As used herein, when a first material is termed as "similar" to a second material, at least 90 weight % of the first and second materials are identical and any variation between the first and second materials comprises less than about 10 weight % of each of the first and second materials.

As used herein, "at least one of A and B" should be understood to mean "only A, only B, or both A and B".

Unless specified or limited otherwise, the terms "attached," "connected," and variations thereof, are used broadly and encompass both direct and indirect attachments, connections, and couplings.

As used herein, the terms "layer,", and "sheet" or variations thereof, are used to describe an article having a thickness that is small relative to its length and width.

As used herein, the term "polymer" refers to both materials prepared from one monomer such as a homopolymer or to materials prepared from two or more monomers such as a copolymer, terpolymer, or the like.

As used herein, the term "heat seal" refers to the formation of a fusion bond between two sheets or layers by suitable heating means.

As used herein, the term "heat-sealing process" refers to a process of sealing two or more surfaces using heat and pressure. A direct contact method of heat-sealing may utilize a constantly heated die or sealing jaws to apply heat to a specific contact area or path to seal or weld the two or more surfaces together. Heat-sealing is used for many applications, including heat seal connectors, thermally activated adhesives, film media, plastic ports, and foil sealing. The direct contact method of heat-sealing may utilize one or more heated bars, irons, dies, and jaws which contact the material to heat an interface and form a bond. The bars, irons, dies and jaws may have various configurations, and may be covered with a release layer or utilize various slick interposer materials (e.g., Teflon films) to prevent sticking to the two or more surfaces during the heat-sealing process.

As used herein, the term "line of weakness" refers to a continuous or non-continuous series of holes, vents, slits, slots, perforations, notches, punctures, orifices, openings, inlets, channels, etc., in the surface of or through sheet. Line of weakness may also be referred to as "score line". A line of weakness may have varying depths. Its depth may extend from the first surface of a sheet to the second surface of the sheet (i.e., throughout the entire thickness of the sheet). Alternatively, its depth may extend from about 50% to about 95% of the thickness of a sheet. The line of weakness may provide a weakened tear point(s). The line of weakness may be formed by mechanical means (e.g., using a cutting blade), by chemical means (e.g., using solvents), by thermal means (e.g., by optical ablation), or by other means known in the art.

As used herein, the term "air permeability" refers a measure of ease with which air passes through a layer. The term "air permeable" refers to a layer that permits the passage of sufficient air through the layer.

The present disclosure provides a warming blanket for warming a patient. The warming blanket includes a first sheet including a first major surface of the warming blanket. The warming blanket further includes a second sheet including a second major surface of the warming blanket opposite to the first major surface. The second sheet is sealingly joined to the first sheet to form one or more inflatable portions between the first sheet and the second sheet. The warming blanket further includes an adhesive layer disposed on at least a portion of the first major surface of the first sheet. The adhesive layer includes an adhesive. The warming blanket further includes a liner assembly disposed on the adhesive layer opposite to the first major surface and fully covering the adhesive layer. The liner assembly includes a plurality of release liners delimited from each other and releasably bonded to the adhesive layer, such that each release liner is independently removable from the liner assembly to expose a corresponding portion of the adhesive layer. Each of the first sheet, the adhesive layer, and the plurality of release liners is air-permeable.

Conventional convective blankets are generally designed to accommodate a specific position (e.g., a surgical position) of the patient. Consequently, conventional convective blankets with different designs may be required for different positions of the patient. In some positions of the patient, multiple conventional convective blankets having different designs may be required to effectively accommodate and cover the patient.

However, in certain positions of the patient, the multiple conventional convective blankets may not effectively accommodate and cover the patient. Further, the multiple conventional convective blankets may fall off the patient due to inadequate securement. Specifically, the multiple conventional convective blankets may not properly secure to the patient (for example, to a skin of the patient, clothes of the patient, or various health care equipment, such as a bed). Furthermore, health care facilities may have limited conventional convective blankets having different designs. Effectively accommodating and covering the patient in different positions may not be possible with the limited conventional convective blankets.

The warming blanket of the present disclosure may cover the patient in a variety of different positions (e.g., different surgical positions). In other words, a single unit of the warming blanket may be used to cover the patient in the multiple different positions. Further, the warming blanket of the present disclosure may conform to the patient and cover as much surface area as possible or required in the multiple different positions of the patient. Moreover, in certain positions of the patient, the warming blanket of the present disclosure may cover the patient more effectively as compared to the conventional convective blankets.

Further, the warming blanket of the present disclosure may firmly secure the patient via the corresponding portions of the adhesive layer exposed by independent removal of the plurality of release liners from the liner assembly. In some cases, the plurality of release liners may be detachably joined to each other along respective lines of weakness and may be independently detached from each other along the respective lines of weakness. In some examples, the warming blanket of the present disclosure may further include at least one blanket line of weakness, and one line of weakness of the liner assembly may at least partially extend along the at least one blanket line of weakness. Therefore, the warming blanket may be split along the at least one blanket line of weakness to allow access to various portions of the patient. Furthermore, the at least one blanket line of weakness may allow the warming blanket to better cover the patient in the multiple different positions.

In some cases, the adhesive layer may be patterned. For example, the adhesive layer may include non-adhesive portions between the adjacent adhesive portions. The plurality of release liners may not be detachably attached to the adhesive layer at the non-adhesive portions. Consequently, the non-adhesive portions may facilitate independent removal of the plurality of release liners from the liner assembly. In some other cases, the plurality of release liners may include other features, such as a pull tab, to facilitate independent removal of the plurality of release liners from the liner assembly.

The warming blanket may be used to cover the patient in the multiple different positions, may firmly secure to the patient, and may allow access to certain portions of the patient during a medical procedure (e.g., a surgery).

The warming blankets illustrated and discussed below are inflatable. That is, their structures, flaccid when not in use, tauten when receiving a stream of pressurized air.

Figure 2:
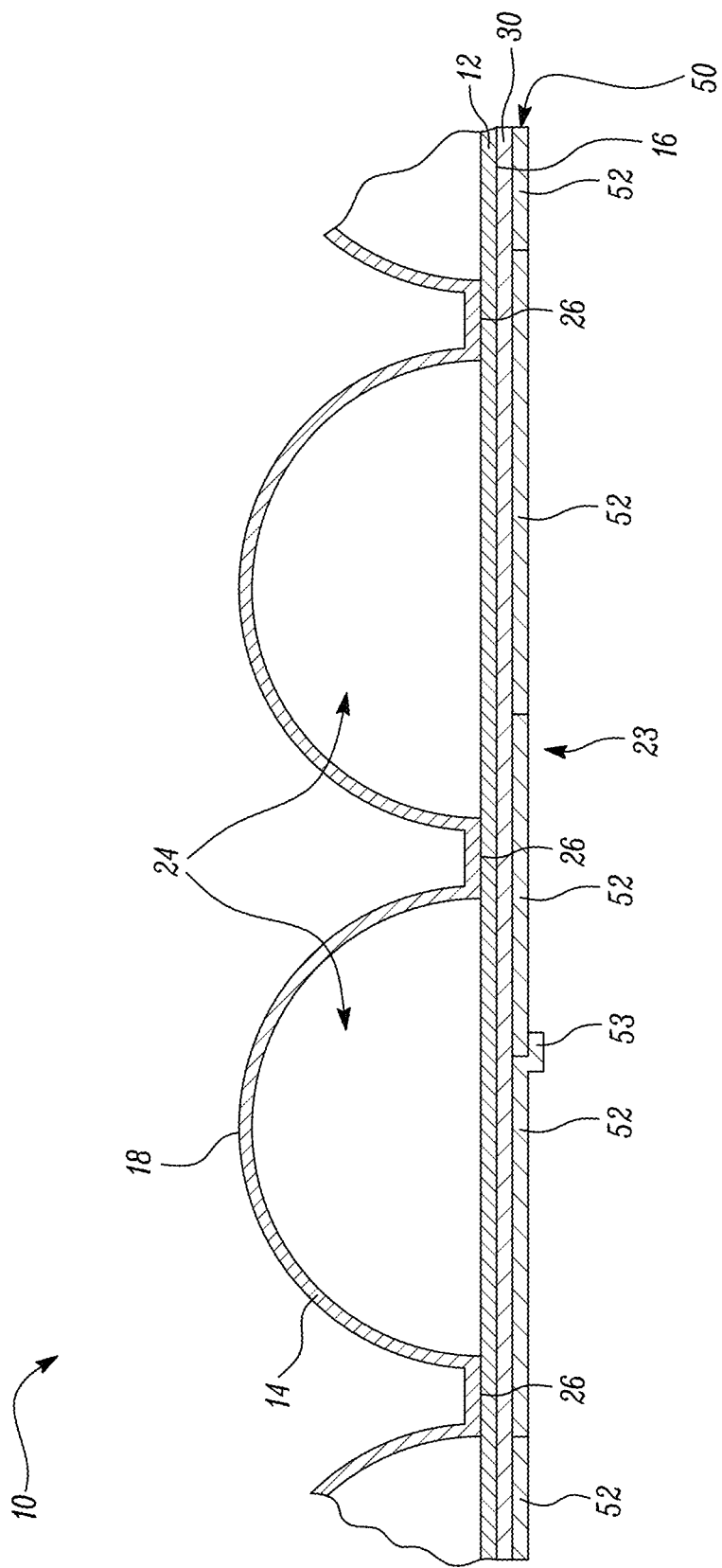
FIG. 2 is a schematic cross-sectional view of a portion of the warming blanket taken along a line 1-1 of FIG. 1.

Referring now to Figures, FIGS. 1 and 2 illustrate a warming blanket 10 for warming a patient according to an embodiment of the present disclosure. Specifically, FIG. 1 illustrates a schematic perspective view of the warming blanket 10, and FIG. 2 illustrates a schematic cross-sectional view of a portion of the warming blanket 10 taken along a line 1-1 of FIG. 1.

The warming blanket 10 may be a forced-air warming (FAW) blanket that is designed keep patients at a normal core body temperature (e.g., about 37° C.). The warming blanket 10 may be used, for example, during all phases of a surgery to prevent emergency medical conditions, such as hypothermia.

In the illustrated embodiment of FIG. 1, the warming blanket 10 has a substantially rectangular shape. However, the warming blanket 10 may have any suitable shape, such as a circular, a triangular, pentagonal, or any other suitable polygonal shape. The warming blanket 10 may conform to a body of the patient. Specifically, the warming blanket 10 may conform to at least a portion of the body of the patient.

Referring to FIGS. 1 and 2, the warming blanket 10 includes a first sheet 12 (shown in FIG. 2). The first sheet 12 includes a first major surface 16 of the warming blanket 10. The warming blanket 10 further includes a second sheet 14. The second sheet 14 includes a second major surface 18 of the warming blanket 10 opposite to the first major surface 16.

The second sheet 14 is typically air impermeable. In other words, the second sheet 14 may not allow substantial passage of air therethrough. Therefore, the second sheet 14 may face away from the patient when the warming blanket 10 is deployed for use. The first sheet 12 is air permeable. In other words, the first sheet 12 may allow substantial passage of air therethrough. The first sheet 12 may be air permeable due to apertures/perforations formed on the first sheet 12, due to a construction of the first sheet 12, due to a material of the first sheet 12, and so forth. Therefore, the first major surface 16 of the first sheet 12 may face the patient when the warming blanket 10 is deployed for use.

The second sheet 14 is sealingly joined to the first sheet 12 to form one or more inflatable portions 24 between the first sheet 12 and the second sheet 14. In other words, the first sheet 12 and the second sheet 14 are sealed together to form the one or more inflatable portions 24 therebetween. The one or more inflatable portions 24 may be formed such that air may flow between adjacent inflatable portions 24 and uniformly distribute across the one or more inflatable portions 24.

The first sheet 12 and the second sheet 14 may be sealingly joined together by using heat seals, adhesives, ultrasonic welds, or any other equivalent techniques. The first sheet 12 and the second sheet 14 may be sealingly joined together at their peripheries and at a plurality of stake points 26 (shown in FIG. 2) within their peripheries to form the one or more inflatable portions 24.

In the illustrated embodiment of FIG. 1, the warming blanket 10 further includes an inlet 28 disposed in fluid communication with the one or more inflatable portions 24 and configured to receive air therein. In other words, the one or more inflatable portions 24 between the first sheet 12 and the second sheet 14 may be inflated with warm air via the inlet 28. In the illustrated embodiment of FIG. 1, the inlet 28 is formed on the second sheet 14. However, the inlet 28 may be formed at any suitable position, as per desired application attributes. For example, the inlet 28 may be formed at peripheries of the first and second sheets 12, 14, or at corners of the first and second sheets 12, 14. The inlet 28 may be connectable with a hose of a warming unit (not shown) to inflate the one or more inflatable portions 24 with warm air.

The warming blanket 10 further includes an adhesive layer 30 (shown in FIG. 2) disposed on at least a portion of the first major surface 16 of the first sheet 12. The adhesive layer 30 includes an adhesive. The adhesive may be any suitable adhesive, as per desired application attributes. For example, the adhesive may be skin friendly and easy to remove without leaving residue. Examples of the adhesive include, but are not limited to, pressure-sensitive adhesives, epoxy adhesives, polyurethane adhesives, and polyimide adhesives.

In some embodiments, the adhesive layer 30 covers at least 25% of the first major surface 16. The adhesive layer 30 may cover at least 30%, at least 35%, at least 40%, at least 45%, at least 50%, at least 55%, at least 60%, at least 65%, at least 70%, at least 75%, at least 80%, at least at least 85%, at least 90%, or at least 95% of the first major surface 16. In some other embodiments, the adhesive layer 30 covers 100% of the first major surface 16. In other words, in some embodiments, the adhesive layer 30 is disposed on an entirety of the first major surface 16.

The warming blanket 10 further includes a liner assembly 50 (shown in FIG. 2) disposed on the adhesive layer 30 opposite to the first major surface 16 and fully covering the adhesive layer 30. In some embodiments, the liner assembly 50 may have greater dimensions than the first major surface 16 to fully cover the adhesive layer 30. In some embodiments, the liner assembly 50 may have smaller dimensions than the first major surface 16 to fully cover the adhesive layer 30 (for example, when the adhesive layer 30 covers less than 100% of the first major surface 16). In some embodiments, the liner assembly 50 is substantially coextensive with the first major surface 16 of the first sheet 12. In other words, in some embodiments, the liner assembly 50 and the first major surface 16 extend over a same area. The liner assembly 50 may protect the adhesive layer 30 from contaminants, such as dust, debris, and the like, prior to use of the warming blanket 10.

The liner assembly 50 includes a plurality of release liners 52 delimited from each other and releasably bonded to the adhesive layer 30, such that each release liner 52 is independently removable from the liner assembly 50 to expose a corresponding portion of the adhesive layer 30. In other words, each release liner 52 from the plurality of release liners 52 may be independently or individually removed from the liner assembly 50 and the adhesive layer 30 to expose the corresponding portion of the adhesive layer 30. In one example, the plurality of release liners 52 may be separate from each other.

One or more of the plurality of release liners 52 may be independently removed from the liner assembly 50 to expose corresponding portions of the adhesive layer 30 based upon a position of the patient. The warming blanket 10 may be removably secured to the patient via the corresponding portions of the adhesive layer 30 exposed by removing one or more of the plurality of release liners 52.

Each of the plurality of release liners 52 may include any suitable material, such as Polyethylene Terephthalate (PET), High-Density Polyethylene (HDPE), Polyvinyl Chloride (PVC), Polypropylene (PP), and the like. In some embodiments, each of the plurality of release liners 52 includes a non-woven material. In some embodiments, the non-woven material includes at least one of cotton, polyester, polypropylene, polyamide, and rayon. The non-woven material of each of the plurality of release liners 52 may be soft, thereby providing improved comfort to the patient during use of the warming blanket 10.

Each of the plurality of release liners 52 may include any suitable features to be independently removed from the liner assembly 50. For example, in the illustrated embodiment of FIG. 2, one release liner 52 from the plurality of release liners 52 overlaps with an adjacent release liner 52, such that an overlapping portion 53 is formed that is not bonded to the adhesive layer 30. The overlapping portion 53 may be gripped to remove the one release liner 52 from the liner assembly 50 and the adhesive layer 30. In another example, the plurality of release liners 52 may include pull tabs that may be gripped and pulled, such that one or more of the plurality of release liners 52 may be independently removed from the liner assembly 50.

Each of the first sheet 12, the adhesive layer 30, and the plurality of release liners 52 is air-permeable. In other words, air may pass through each of the first sheet 12, the adhesive layer 30, and the plurality of release liners 52. In some embodiments, an air permeability of each of the first sheet 12, the adhesive layer 30, and the plurality of release liners 52 is from about 5 cubic feet per minute (CFM) to about 100 CFM.

In one example, the first sheet 12 and each of the plurality of release liners 52 may be made of an air permeable material, and the adhesive layer 30 may be patterned to allow airflow therethrough. In another example, the first sheet 12, each release liner 52, and the adhesive layer 30 may include at least some aligned perforations to allow airflow therethrough. As discussed above, the one or more inflatable portions 24 of the warming blanket 10 between the first sheet 12 and the second sheet 14 may be inflated with the warm air via the inlet 28. Thus, the warm air may fluidly communicate with and warm the patient through the first sheet 12, the adhesive layer 30, and at least one of the plurality of release liners 52.

Since each of the first sheet 12, the adhesive layer 30, and the plurality of release liners 52 is air-permeable, the first sheet 12, the adhesive layer 30, and the plurality of release liners 52 may allow an airflow of the warm air from the inflatable portions 24 of the warming blanket 10 to the patient. In other words, the warm air may pass through each of the first sheet 12, the adhesive layer 30, and the plurality of release liners 52 from the inflatable portions 24 and emit from a patient facing side 23 of the warming blanket 10 to warm the patient.

Figure 3:
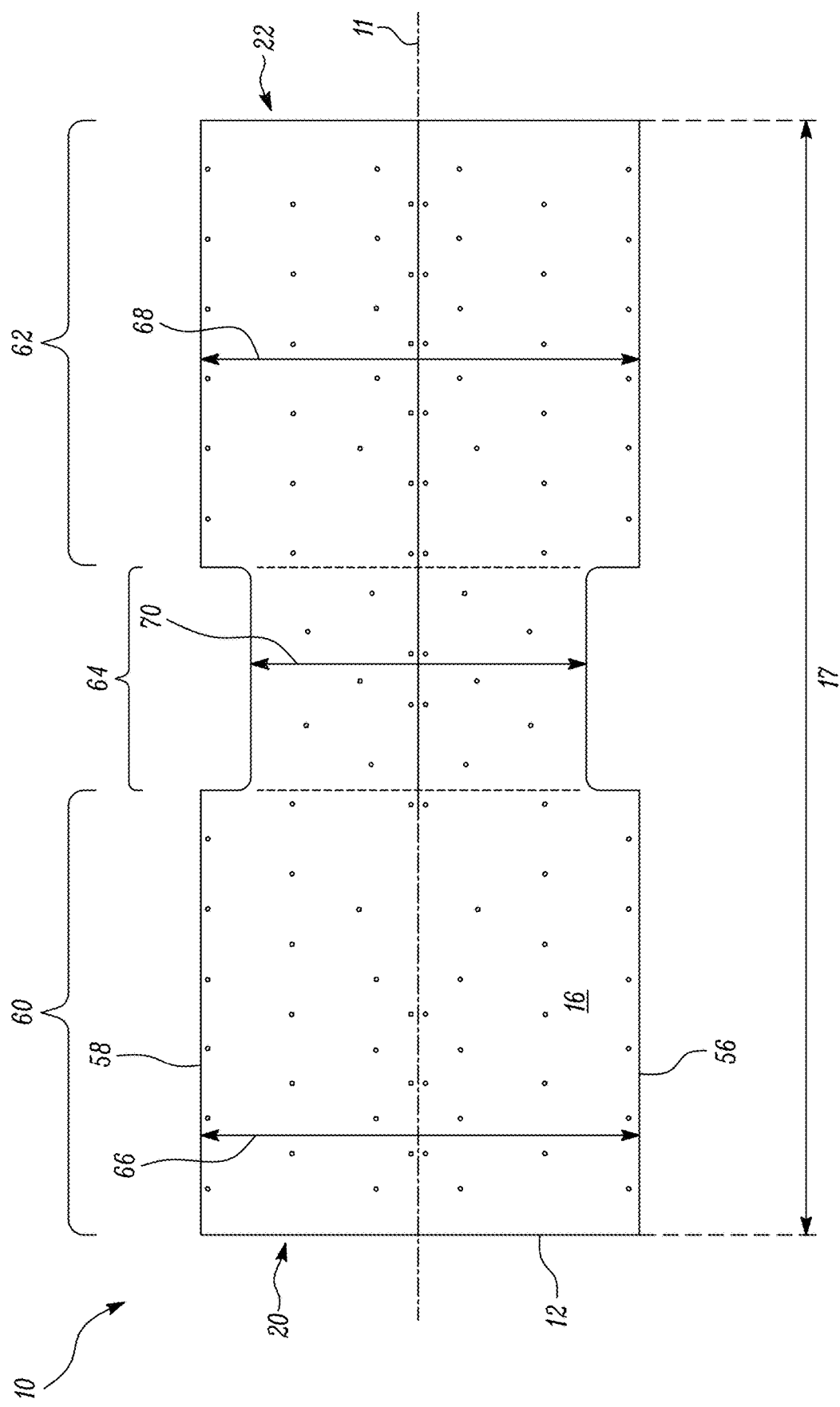
FIG. 3 is a schematic bottom view of the warming blanket of FIG. 1.

FIG. 3 illustrates a schematic bottom view of the warming blanket 10 according to an embodiment of the present disclosure. The liner assembly 50 and the adhesive layer 30 (both shown in FIG. 2) are not shown in FIG. 3 for illustrative purposes.

In the illustrated embodiment of FIG. 3, the first major surface 16 extends along a longitudinal axis 11 between a first end 20 to an opposing second end 22. Further, in the illustrated embodiment of FIG. 3, the first major surface 16 includes a first transverse edge 56 and an opposing second transverse edge 58. As shown in FIG. 3, in some embodiments, each of the first transverse edge 56 and the second transverse edge 58 extends from the first end 20 to the second end 22. In some examples, the warming blanket 10 may extend along the longitudinal axis 11 (also shown in FIG. 1) from the first end 20 to the second end 22.

In the illustrated embodiment of FIG. 3, the first major surface 16 further includes a first surface portion 60, a second surface portion 62, and a third surface portion 64. The first surface portion 60 extends from the first end 20 of the first major surface 16 and has a first width 66 from the first transverse edge 56 to the second transverse edge 58. The second surface portion 62 extends from the second end 22 of the first major surface 16 and has a second width 68 from the first transverse edge 56 to the second transverse edge 58. Further, the third surface portion 64 is disposed between the first surface portion 60 and the second surface portion 62 with respect to the longitudinal axis 11. The third surface portion 64 has a third width 70 from the first transverse edge 56 to the second transverse edge 58 less than each of the first width 66 and the second width 68. Each of the first width 66, the second width 68, and the third width 70 may be substantially normal to the longitudinal axis 11.

Further, in the illustrated embodiment of FIG. 3, the first major surface 16 includes a length 17 along the longitudinal axis 11. In other words, in the illustrated embodiment of FIG. 3, the first major surface 16 has the length 17 between the first end 20 and the second end 22 along the longitudinal axis 11. The length 17 may be a sum of lengths of the first surface portion 60, the second surface portion 62, and the third surface portion 64 along the longitudinal axis 11. In some embodiments, the length 17 may be greater than about two times of each of the first width 66 and the second width 68. In some embodiments, the length 17 may be greater than about three times of the third width 70.

Figure 4A:
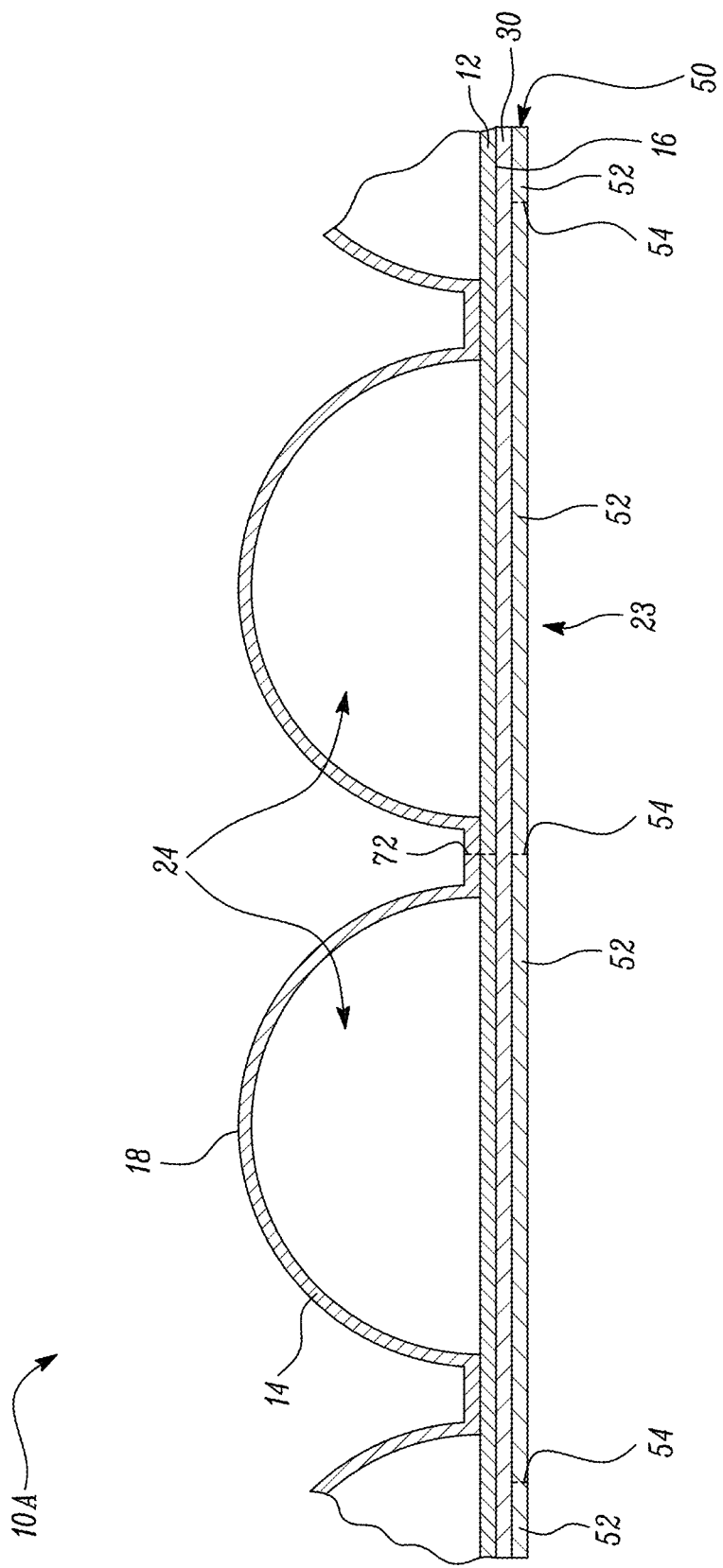
FIG. 4A is a schematic cross-sectional view of a portion of a warming blanket according to another embodiment of the present disclosure.
Figure 4B:
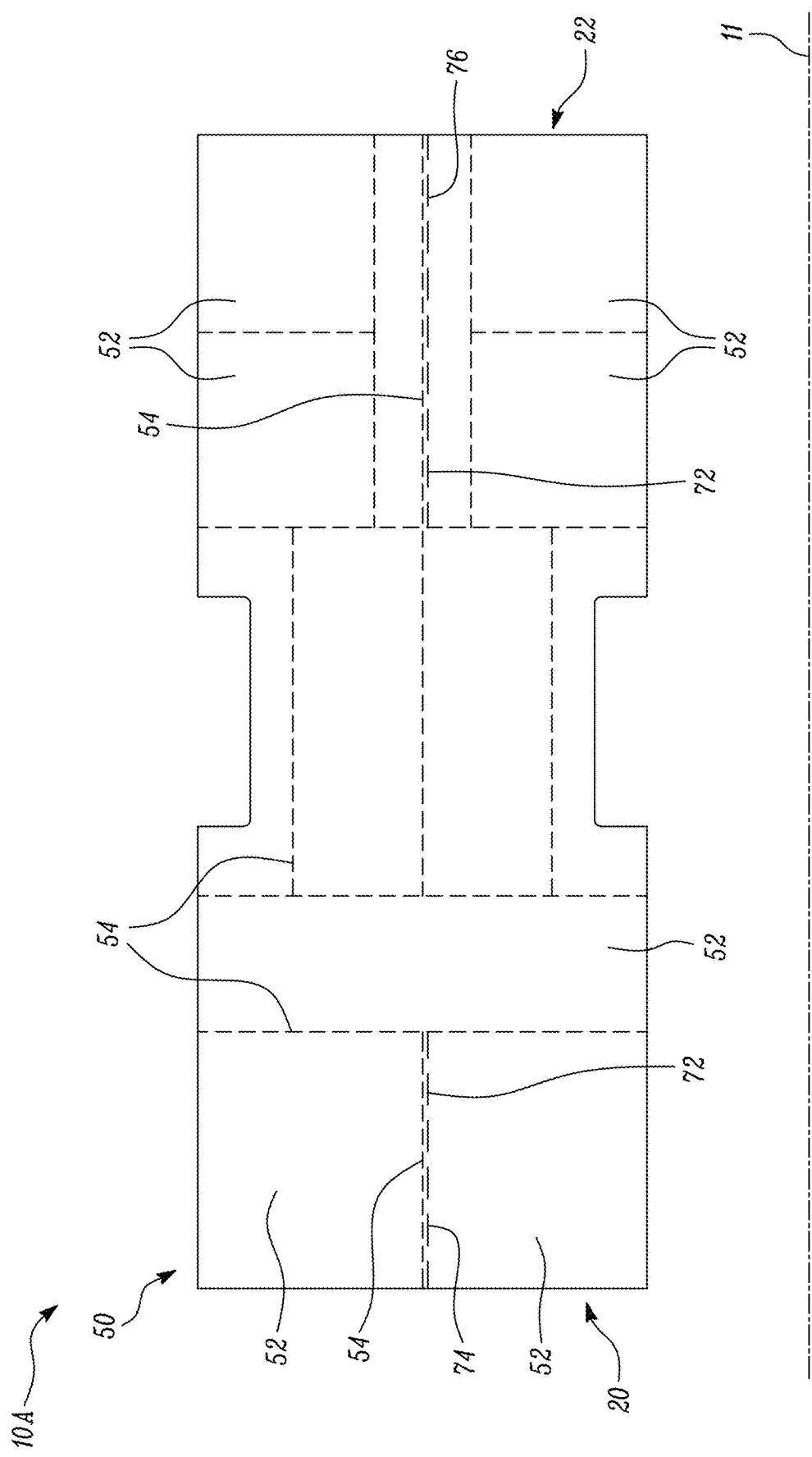
FIG. 4B is a schematic bottom view of the warming blanket of FIG. 4A.

FIGS. 4A and 4B illustrate a warming blanket 10A according to another embodiment of the present disclosure. Specifically, FIG. 4A illustrates a cross-sectional view of a portion of a warming blanket 10A, and FIG. 4B illustrates a bottom view of the warming blanket 10A.

The warming blanket 10A is similar to the warming blanket 10 shown in FIGS. 1-3, with like elements designated by like numbers. However, the warming blanket 10A has a different configuration of the liner assembly 50 as compared to the warming blanket 10. Further, the warming blanket 10A includes additional features allowing the warming blanket 10A to be split open.

Referring to FIGS. 4A and 4B, in some embodiments, the liner assembly 50 includes a plurality of lines of weakness 54 (shown by dashed lines in FIGS. 4A and 4B). Further, in some embodiments, adjacent release liners 52 from the plurality of release liners 52 are detachably joined to each other along respective lines of weakness 54 from the plurality of lines of weakness 54. The plurality of lines of weakness 54 may delimit the plurality of release liners 52 from each other. Each release liner 52 may be independently removable from the liner assembly 50 and detached from an adjacent release liner 52 via the respective lines of weakness 54.

In some embodiments, each line of weakness 54 includes at least one of a slit, a perforation, and a score. In other words, in some embodiments, the liner assembly 50 may be slitted, perforated, or scored to form the plurality of lines of weakness 54. As shown in FIG. 4B, in some embodiments, at least two lines of weakness 54 from the respective lines of weakness 54 intersect each other.

In the illustrated embodiment of FIG. 4A, the first sheet 12 and second sheet 14 further include at least one blanket line of weakness 72 (shown by dashed lines in FIGS. 4A and 4B). Further, one line of weakness 54 from the plurality of lines of weakness 54 of the liner assembly 50 at least partially extends along the at least one blanket line of weakness 72. In FIG. 4B, the at least one blanket line of weakness 72 is shown as being slightly offset from the one line of weakness 54 for illustrative purposes. It may be noted that the at least one blanket line of weakness 72 may be substantially aligned with the one line of weakness 54. Therefore, the warming blanket 10A may allow different portions of the body of the patient to be accessed by a health care personnel. In other words, the at least one blanket line of weakness 72 may allow the health care personnel to access the different portions of the body of the patient. Furthermore, the at least one blanket line of weakness 72 may allow the warming blanket 10A to better cover the patient in different positions.

In some embodiments, the at least one blanket line of weakness 72 includes a first blanket line of weakness 74 (shown in FIG. 4B) extending from the first end 20 of the first major surface 16, and a second blanket line of weakness 76 (shown in FIG. 4B) extending from the second end 22 of the first major surface 16 and spaced apart from the first blanket line of weakness 74. The first blanket line of weakness 74 and the second blanket line of weakness 76 may allow the warming blanket 10A to be split along opposite sides, and therefore may allow the health care personnel to access the different portions of the body of the patient.

Figure 5:
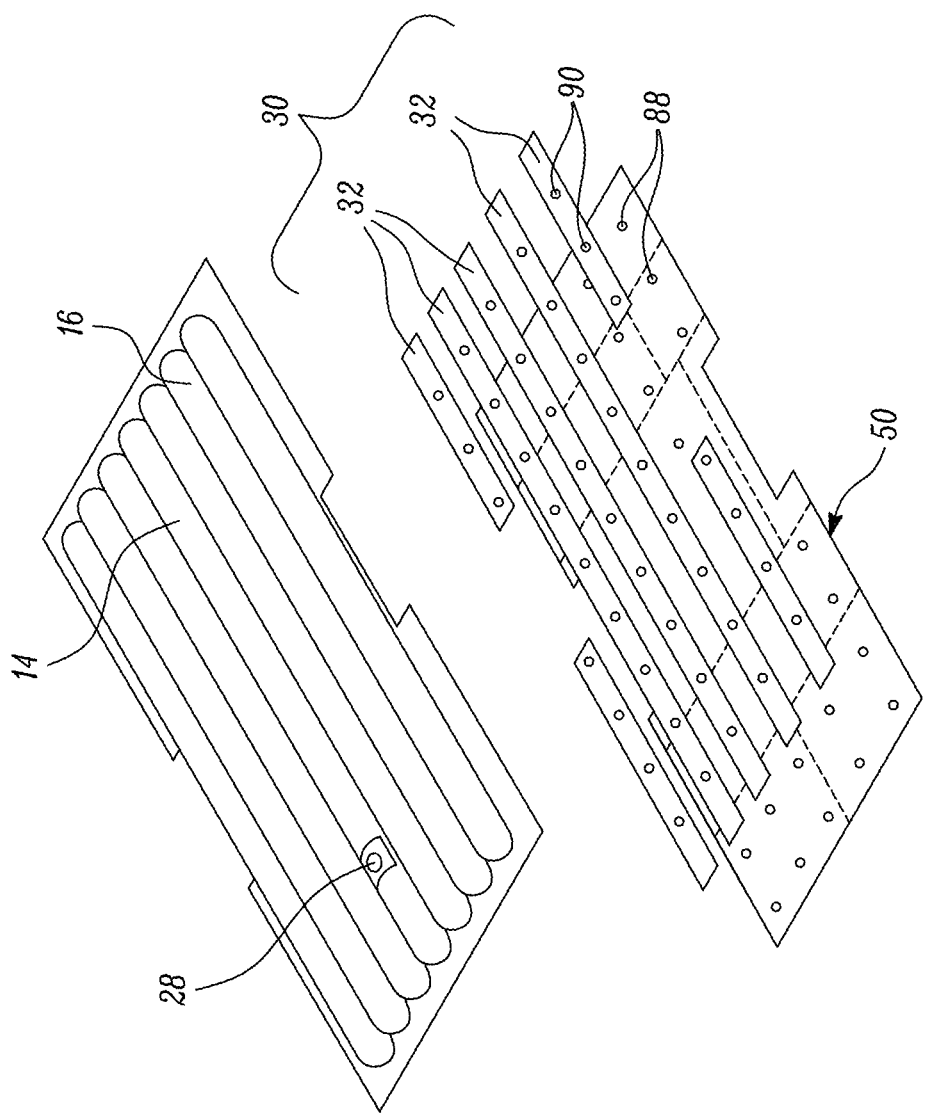
FIG. 5 is a schematic exploded perspective view of a warming blanket according to another embodiment of the present disclosure.
Figure 6:
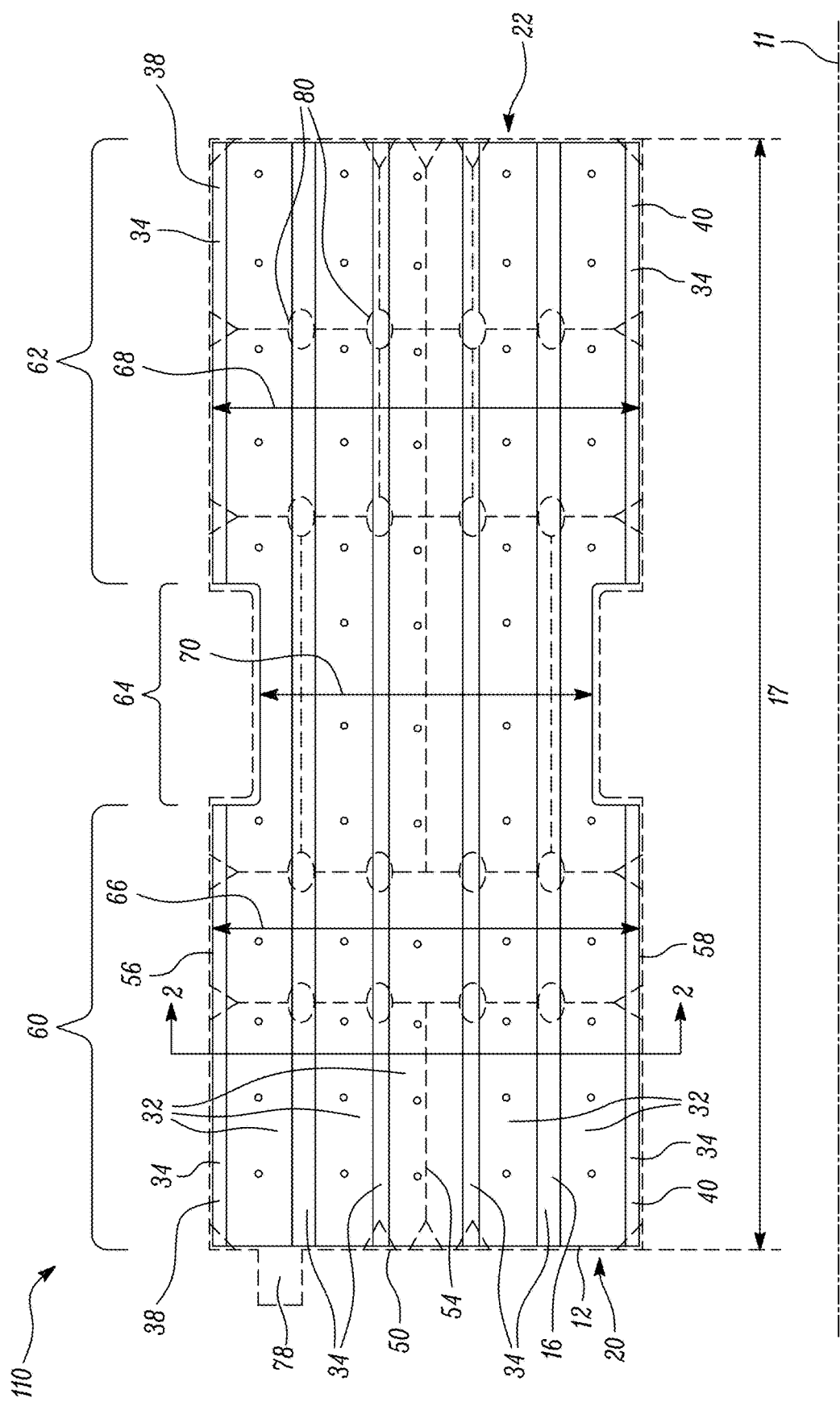
FIG. 6 is a schematic bottom view of the warming blanket of FIG. 5.

FIGS. 5 and 6 illustrate a warming blanket 110 according to an embodiment of the present disclosure. Specifically, FIG. 5 illustrates a schematic exploded perspective view of the warming blanket 110 and FIG. 6 illustrates a schematic bottom view of the warming blanket 110.

The warming blanket 110 is similar to the warming blanket 10 shown in FIGS. 1-3, with like elements designated by like numerals. However, the warming blanket 110 has a different configuration of the adhesive layer 30 and the liner assembly 50 as compared to the warming blanket 10. The liner assembly 50 of the warming blanket 110 is depicted as transparent and by dashed lines in FIG. 6 for illustrative purposes.

Referring to FIGS. 5 and 6, in some embodiments, the adhesive layer 30 includes a plurality of adhesive portions 32 spaced apart from each other, such that the first major surface 16 (shown in FIG. 6) of the first sheet 12 includes a plurality of non-adhesive portions 34 alternating with the plurality of adhesive portions 32. Specifically, in the illustrated embodiment of FIG. 6, the plurality of adhesive portions 32 includes five adhesive portions 32 spaced apart from each other. The plurality of non-adhesive portions 34 may be defined by spacings between the plurality of adhesive portions 32. Each non-adhesive portion 34 is free of the adhesive. In other words, each non-adhesive portion 34 does not include the adhesive of the adhesive layer 30.

Further, in the illustrated embodiment of FIG. 6, each adhesive portion 32 extends along the longitudinal axis 11 of the first major surface 16 from the first end 20 of the first major surface 16 to the opposing second end 22 of the first major surface 16. Moreover, in the illustrated embodiment of FIG. 6, each non-adhesive portion 34 extends at least partially along the longitudinal axis 11 of the first major surface 16. Specifically, in some embodiments, a length of each non-adhesive portion 34 is at least 30% of the length 17 of the first major surface 16 along the longitudinal axis 11. In some embodiments, the length of each non-adhesive portion 34 may be at least 10%, at least 15%, at least 20%, or at least 25% of the length 17 of the first major surface 16 along the longitudinal axis 11. As shown in FIG. 6, in some embodiments, the length of at least one of the plurality of non-adhesive portions 34 is substantially equal to the length 17 of the first major surface 16.

In some embodiments, the plurality of non-adhesive portions 34 forms at most 75% of the first major surface 16. In some embodiments, the plurality of non-adhesive portions 34 may form at most 70%, at most 65%, at most 60%, at most 55%, at most 50%, at most 45%, at most 40%, at most 35%, at most 30%, at most 25%, at most 20%, at most 15%, at most 10%, or at most 5% of the first major surface 16. For example, in cases where the adhesive layer 30 covers about 40% of the first major surface 16, the plurality of non-adhesive portions 34 may form about 60% of the first major surface 16.

In some embodiments, the plurality of adhesive portions 32 may cover at least 25% of the first major surface 16. In some embodiments, the plurality of adhesive portions 32 may cover at least 30%, at least 35%, at least 40%, at least 45%, at least 50%, at least 55%, at least 60%, at least 65%, at least 70%, at least 75%, at least 80%, at least 85%, at least 90%, or at least 95% of the first major surface 16.

In the illustrated embodiment of FIG. 6, each non-adhesive portion 34 has a substantially rectangular shape. Further, in the illustrated embodiment of FIG. 6, at least one of the plurality of adhesive portions 32 has a substantially rectangular shape. However, in some other embodiments, each adhesive portion 32 and each non-adhesive portion 34 may have any suitable shape, such as a circular, a triangular, or any suitable polygonal shape, depending on desired application attributes.

In the illustrated embodiment of FIG. 6, the plurality of non-adhesive portions 34 includes a set of first non-adhesive edge portions 38 extending along the first transverse edge 56 and a set of second non-adhesive edge portions 40 extending along the second transverse edge 58. Specifically, in the illustrated embodiment of FIG. 6, each first non-adhesive edge portion 38 extends partly along the first transverse edge 56 and each second non-adhesive edge portion 40 extends partly along the second transverse edge 58. In the illustrated embodiment of FIG. 6, each non-adhesive portion 34 disposed between the set of first non-adhesive edge portions 38 and the set of second non-adhesive edge portions 40 extends from the first end 20 of the first major surface 16 to the second end 22 of the first major surface 16.

More specifically, in the illustrated embodiment of FIG. 6, the set of first non-adhesive edge portions 38 includes a pair of first non-adhesive edge portions 38 spaced apart from each other with respect to the longitudinal axis 11 of the first major surface 16. Furthermore, the set of second non-adhesive edge portions 40 comprises a pair of second non-adhesive edge portions 40 spaced apart from each other with respect to the longitudinal axis 11 of the first major surface 16. The pair of first non-adhesive edge portions 38 and the pair of second non-adhesive edge portions 40 may be spaced apart from each other with respect to the longitudinal axis 11 by the third surface portion 64 of the first major surface 16.

In the illustrated embodiment of FIG. 6, the first surface portion 60 includes one of the pair of first non-adhesive edge portions 38 and one of the pair of second non-adhesive edge portions 40. Further, in the illustrated embodiment of FIG. 6, the second surface portion 62 includes the other of the pair of first non-adhesive edge portions 38 and the other of the pair of second non-adhesive edge portions 40. Furthermore, the third surface portion 64 is at least partially covered by respective adhesive portions 32 from the plurality of adhesive portions 32 at the first transverse edge 56 and the second transverse edge 58.

Figure 7:
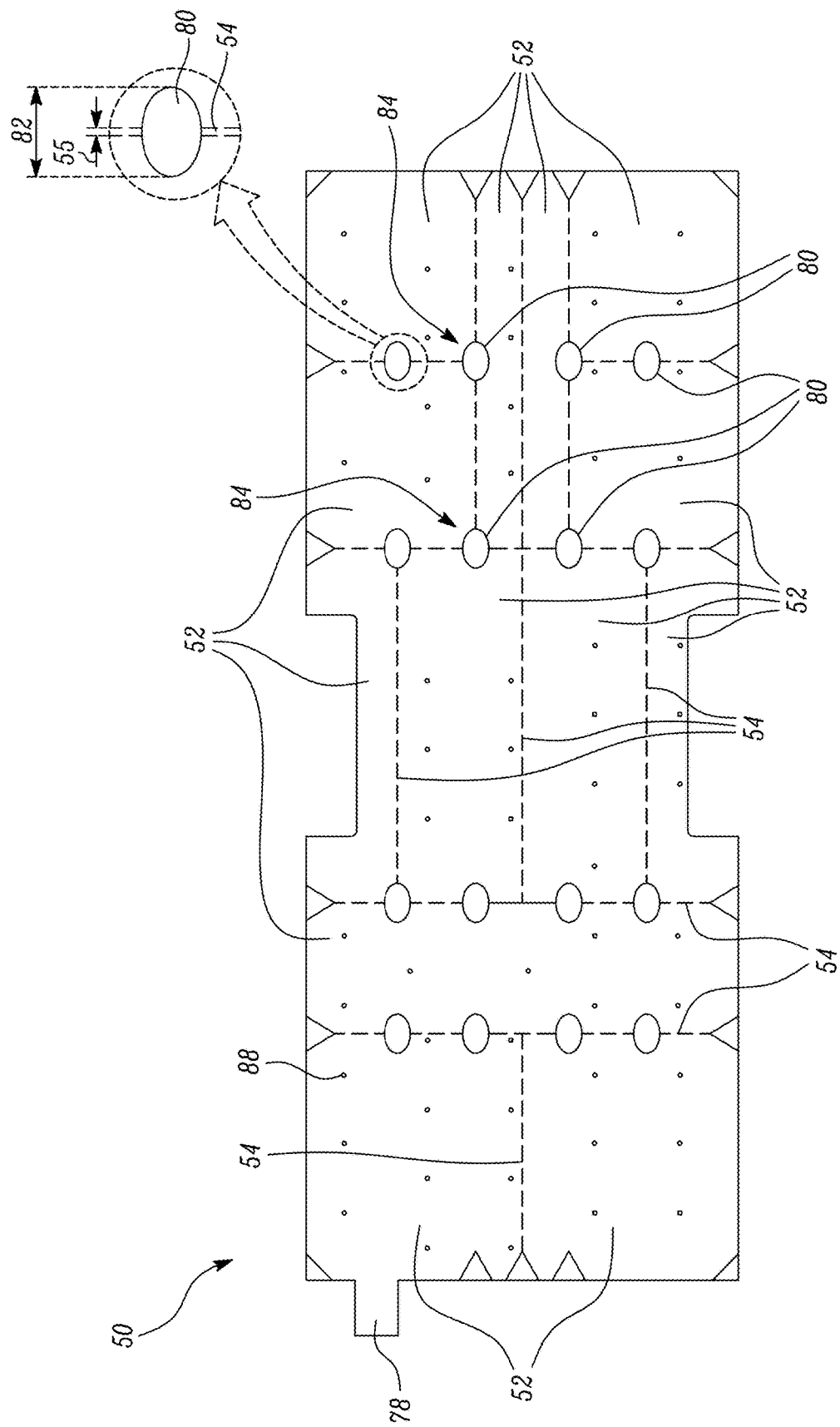
FIG. 7 is a schematic plan view of a liner assembly of the warming blanket of FIG. 6.

FIG. 7 illustrates a schematic plan view of the liner assembly 50 of the warming blanket 110 of FIG. 6 according to an embodiment of the present disclosure.

Referring to FIGS. 6 and 7, the liner assembly 50 includes the plurality of release liners 52. Adjacent release liners 52 from the plurality of release liners 52 are detachably joined to each other along the respective lines of weakness 54 from the plurality of lines of weakness 54.

In some embodiments, at least one release liner 52 from the plurality of release liners 52 extends from the first transverse edge 56 to the second transverse edge 58 to at least partially cover each of the plurality of non-adhesive portions 34. Further, each release liner 52 at least partially covers at least one non-adhesive portion 34. In some embodiments, at least one release liner 52 from the plurality of release liners 52 may cover at least one of the plurality of adhesive portions 32. Specifically, in some embodiments, at least one release liner 52 from the plurality of release liners 52 at least partially covers at least two of the adhesive portions 32.

In some embodiments, at least one release liner 52 from the plurality of release liners 52 includes a pull tab 78 extending therefrom opposite to the first major surface 16 of the first sheet 12. The pull tab 78 may be free of the adhesive of the adhesive layer 30, such that the pull tab 78 may be grippable. The pull tab 78 may be gripped and pulled to independently remove the at least one release liner 52 from the liner assembly 50. The pull tab 78 may facilitate removal of the at least one release liner 52 from the liner assembly 50 of the warming blanket 110.

As shown in FIG. 7, in some embodiments, the liner assembly 50 further includes a plurality of indicators 80 disposed along the plurality of lines of weakness 54. In some embodiments, each indicator 80 is a printed indicator. In some embodiments, each indicator 80 has at least one of an oval shape, a triangular shape, and a circular shape.

In some embodiments, each indicator 80 is at least partially printed on each of the adjacent release liners 52 joined at the respective line of weakness 54. Further, in the illustrated embodiment of FIG. 6, each indicator 80 is aligned with the corresponding non-adhesive portion 34 from the plurality of non-adhesive portions 34. Furthermore, a maximum width 82 of each indicator 80 is greater than a width 55 of each of the respective lines of weakness 54.

As discussed above, in some embodiments, at least two lines of weakness 54 from the respective lines of weakness 54 intersect each other. In the illustrated embodiment of FIG. 7, at least one indicator 80 from the plurality of indicators 80 is disposed at an intersection 84 between the at least two lines of weakness 54.

Figure 8:
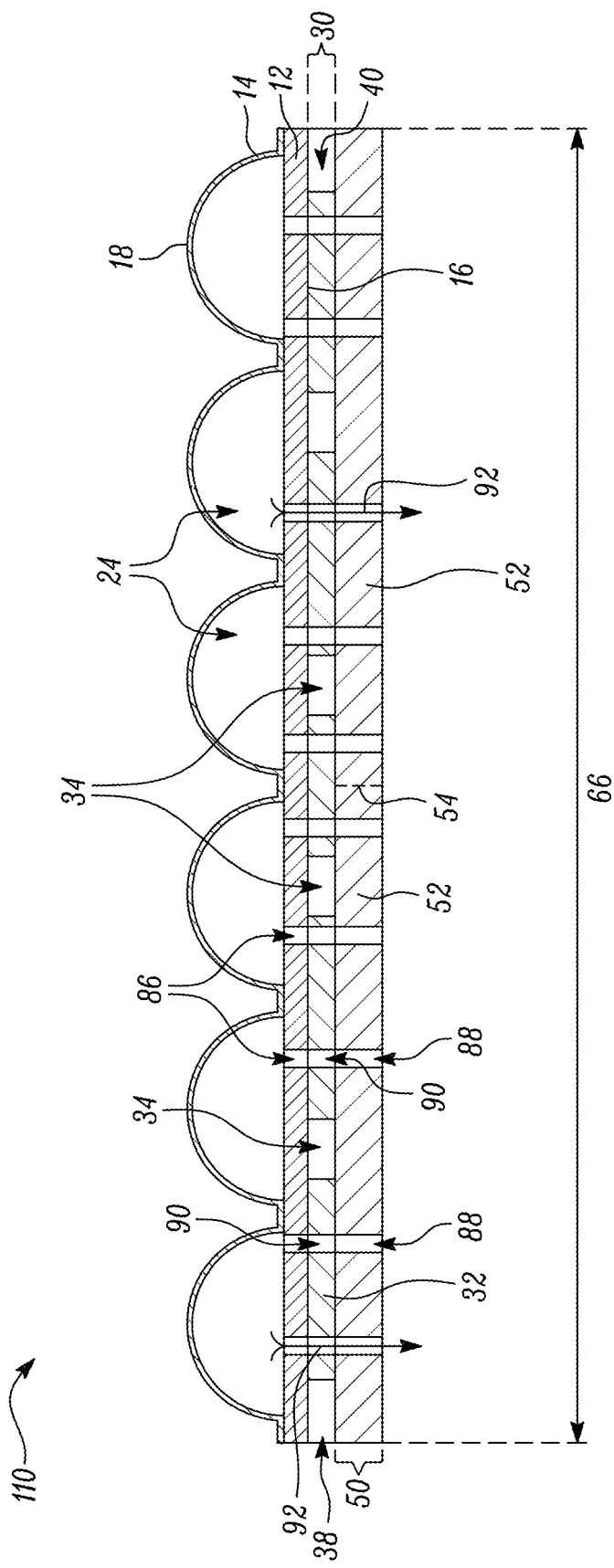
FIG. 8 is a schematic cross-sectional view of the warming blanket taken along a line 2-2 of FIG. 6.

FIG. 8 illustrates a schematic cross-sectional view of the warming blanket 110 taken along a line 2-2 of FIG. 6 according to an embodiment of the present disclosure.

In the illustrated embodiment of FIG. 8, the first sheet 12, the plurality of release liners 52, and the adhesive layer 30 are perforated. Specifically, in the illustrated embodiment of FIG. 8, the first sheet 12 includes a plurality of the first perforations 86, and each release liner 52 includes a plurality of second perforations 88, such that at least some of the second perforations 88 are aligned with corresponding first perforations 86 from the plurality of first perforations 86. Further, the adhesive layer 30 includes a plurality of third perforations 90, such that at least some of the third perforations 90 are aligned with corresponding first perforations 86 from the plurality of first perforations 86 and corresponding second perforations 88 from the plurality of second perforations 88.

In the illustrated embodiment of FIG. 8, at least some perforations from the pluralities of first, second and third perforations 86, 88, 90 are aligned with each other to define an airflow pathway (denoted by arrows 92), through which the warm air from the one or more inflatable portions 24 of the warming blanket 110 may pass. The pluralities of first, second and third perforations 86, 88, 90 may be configured to provide an air permeability of about 5 CFM to about 100 CFM to the first sheet 12, the plurality of release liners 52, and the adhesive layer 30, respectively.

Figure 9:
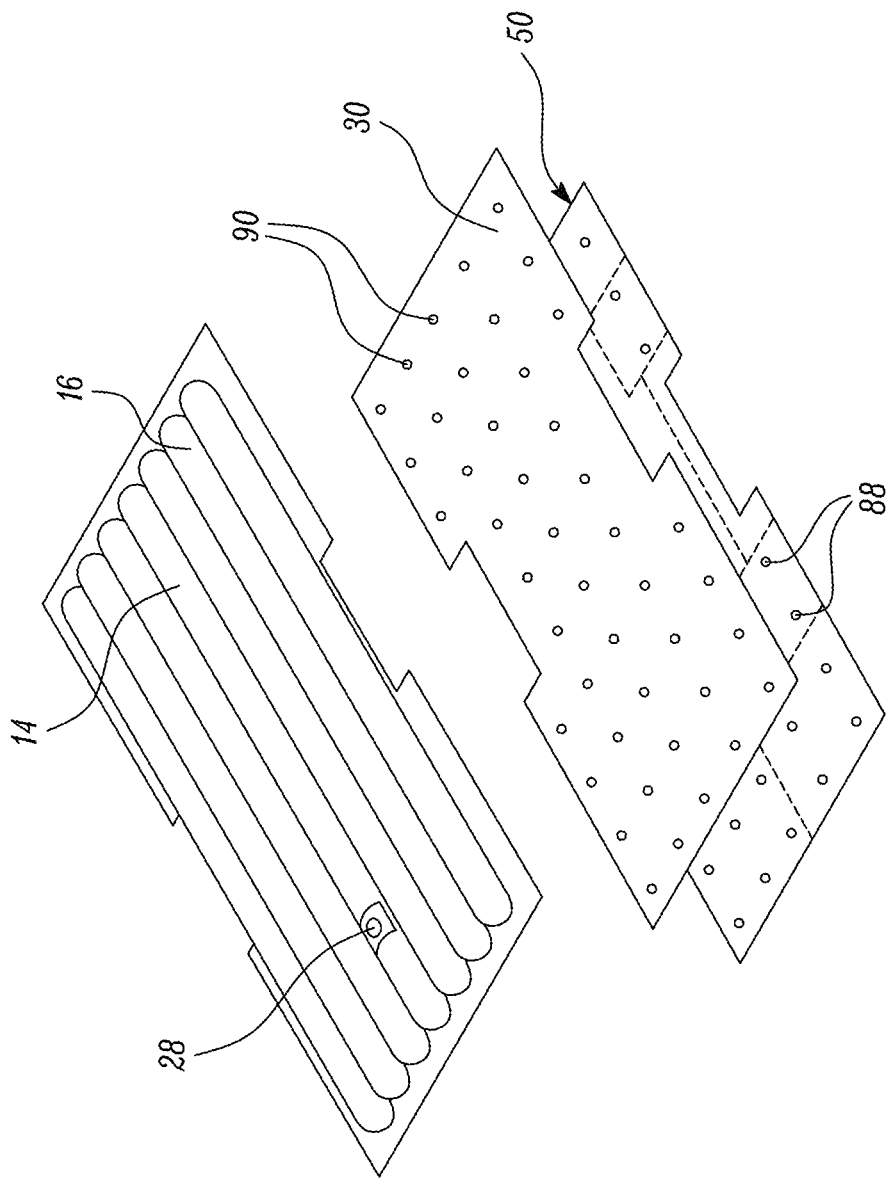
FIG. 9 is a schematic exploded perspective view of a warming blanket according to another embodiment of the present disclosure.
Figure 10:
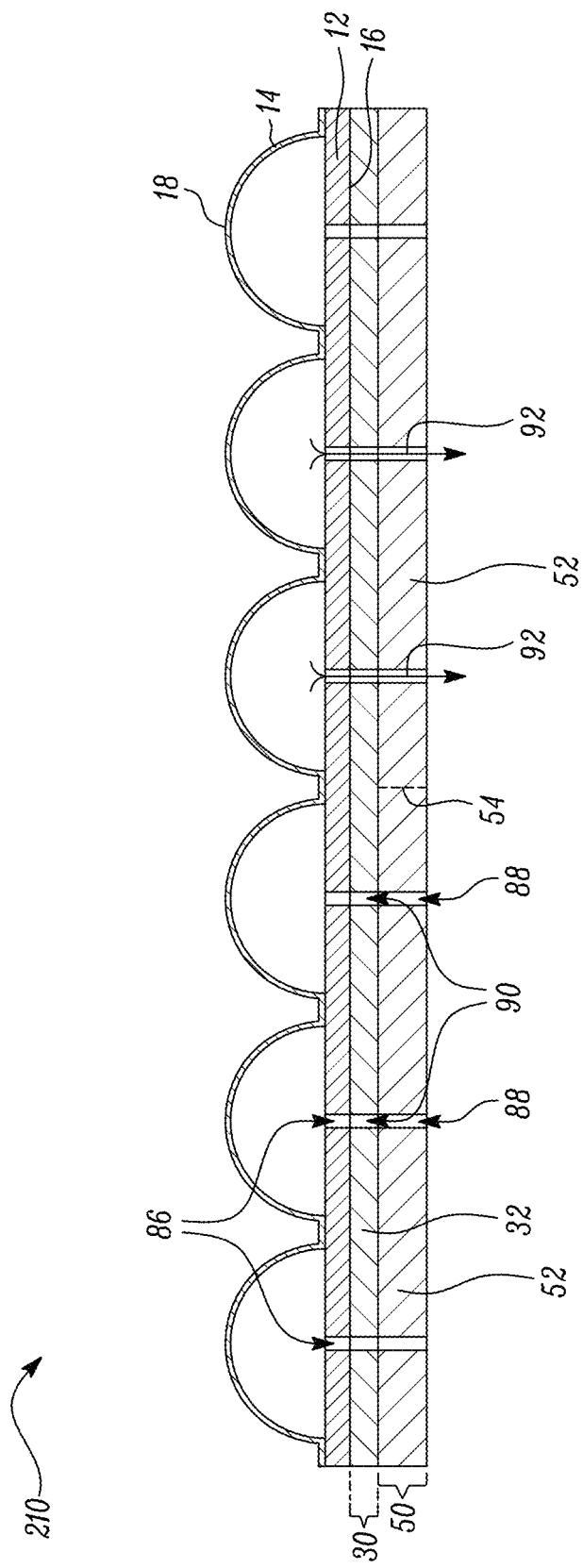
FIG. 10 is a schematic cross-sectional view of the warming blanket of FIG. 9.

FIGS. 9 and 10 illustrate a warming blanket 210 according to an embodiment of the present disclosure. Specifically, FIG. 9 illustrates a schematic exploded perspective view of the warming blanket 210 and FIG. 10 illustrates a schematic cross-sectional view of the warming blanket 210.

The warming blanket 210 is similar to the warming blanket 110 shown in FIGS. 5, 6, and 8, with like elements designated by like numbers. However, the warming blanket 210 has a different configuration of the adhesive layer 30 as compared to the warming blanket 110.

In the illustrated embodiment of FIGS. 9 and 10, the adhesive layer 30 covers 100% of the first major surface 16. Furthermore, the adhesive layer 30 includes the plurality of third perforations 90, such that at least some of the third perforations 90 are aligned with the corresponding first perforations 86 from the plurality of first perforations 86 and the corresponding second perforations 88 from the plurality of second perforations 88. As discussed above, in some embodiments, the pluralities of first, second and third perforations 86, 88, 90 may be configured to provide an air permeability of about 5 CFM to about 100 CFM to the first sheet 12, the plurality of release liners 52, and the adhesive layer 30, respectively.

FIG. 11 illustrates a method 300 of using the warming blanket of the present disclosure according to an embodiment of the present disclosure. The warming blanket has a first sheet, a second sheet sealingly joined to the first sheet to form one or more inflatable portions between the first sheet and the second sheet, an adhesive layer disposed on at least a portion of a first major surface of the first sheet, and a liner assembly disposed on and fully covering the adhesive layer. The liner assembly has a plurality of release liners.

In some embodiments, the method 300 is of using the warming blanket 10 (shown in FIGS. 1-3). In some embodiments, the method 300 is of using the warming blanket 10A (shown in FIGS. 4A and 4B). In some embodiments, the method 300 is of using the warming blanket 110 (shown in FIGS. 5-6 and 8). In some embodiments, the method 300 is of using the warming blanket 210 (shown in FIGS. 9 and 10). The method 300 will be described with reference to the warming blankets 10, 10A, 110, 210. FIGS. 12A-12D illustrate exemplary steps of using the warming blankets 10, 10A, 110, 210. The method 300 will be further described with reference to FIGS. 12A-12D.

At step 302, the method 300 includes removing at least one release liner from the liner assembly to expose at least a portion of the adhesive layer. For example, the method 300 may include removing at least one release liner 52 from the liner assembly 50 to expose at least a portion of the adhesive layer 30. As shown in FIG. 12A, a healthcare personnel 400 may remove the at least one release liner 52 from the liner assembly 50 to expose at least a portion of the adhesive layer 30.

In some embodiments, removing the at least one release liner from the liner assembly further includes detaching the at least one release liner from the liner assembly along one or more respective lines of weakness. For example, the method 300 may include detaching the at least one release liner 52 from the liner assembly 50 along one or more of the respective lines of weakness 54.

In some embodiments, the method 300 further includes splitting each of the first sheet and the second sheet along at least one blanket line of weakness prior to removing the at least one release liner from the liner assembly. For example, the method 300 may further include splitting each of the first sheet 12 and the second sheet 14 along the at least one blanket line of weakness 72 prior to removing the at least one release liner 52 from the liner assembly 50.

At step 304, the method 300 further includes placing the warming blanket on the patient, such that the first major surface faces the patient. For example, the method 300 may further include placing any one of the warming blankets 10, 10A, 110, 210 on the patient, such that the first major surface 16 faces the patient. As shown in FIG. 12B, the warming blanket is placed on a patient 404.

In some embodiments, placing the warming blanket on the patient includes at least partially conforming the warming blanket to the body of the patient. As shown in FIG. 12B, the warming blanket at least partially conforms to a body 402 of the patient 404.

At step 306, the method 300 further includes adhering the warming blanket to a surface via the portion of the adhesive layer exposed by removing the at least one release liner. For example, as shown in FIG. 12C, the healthcare personnel 400 may adhere the warming blanket to a surface 406 via the portion of the adhesive layer 30 exposed by removing the at least one release liner 52 (shown in FIG. 12A). The surface 406 may be a surface of the body 402 of the patient 404 or clothes of the patient 404. In some cases, the surface 406 may be of healthcare equipment.

At step 308, the method 300 further includes inflating the one or more inflatable portions between the first sheet and the second sheet with warm air via an inlet, such that the warm air fluidly communicates with the patient through the first sheet, the adhesive layer, and at least one of the plurality of release liners. For example, the method 300 may further include inflating the one or more inflatable portions 24 between the first sheet 12 and the second sheet 14 with the warm air via the inlet 28, such that the warm air fluidly communicates with the patient through the first sheet 12, the adhesive layer 30, and at least one of the plurality of release liners 52.

As shown in FIG. 12D, the healthcare personnel 400 may connect a hose pipe 408 of a warming unit (not shown) to the inlet 28 of the warming blanket. The inlet 28 of the warming blanket 10 may be connectable with a hose of a warming unit (not shown) to inflate the one or more inflatable portions 24 with warm air. The warming unit may generate warm air and may pump the warm air through the hose pipe 408 into the inlet 28.

Unless otherwise indicated, all numbers expressing feature sizes, amounts, and physical properties used in the specification and claims are to be understood as being modified by the term "about". Accordingly, unless indicated to the contrary, the numerical parameters set forth in the foregoing specification and attached claims are approximations that can vary depending upon the desired properties sought to be obtained by those skilled in the art utilizing the teachings disclosed herein.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

The invention claimed is:

1. A warming blanket for warming a patient, the warming blanket comprising:
 a first sheet comprising a first major surface of the warming blanket;
 a second sheet comprising a second major surface of the warming blanket opposite to the first major surface, wherein the second sheet is sealingly joined to the first sheet to form one or more inflatable portions between the first sheet and the second sheet;
 an adhesive layer disposed on at least a portion of the first major surface of the first sheet, the adhesive layer comprising an adhesive; and
 a liner assembly disposed on the adhesive layer opposite to the first major surface and fully covering the adhesive layer, the liner assembly comprising a plurality of release liners delimited from each other and releasably bonded to the adhesive layer, such that each release liner is independently removable from the liner assembly to expose a corresponding portion of the adhesive layer;
 wherein each of the first sheet, the adhesive layer, and the plurality of release liners is air-permeable.

2. The warming blanket of claim 1, wherein the liner assembly further comprises a plurality of lines of weakness, and wherein adjacent release liners from the plurality of release liners are detachably joined to each other along respective lines of weakness from the plurality of lines of weakness.

3. The warming blanket of claim 2, wherein the adhesive layer comprises a plurality of adhesive portions spaced apart from each other, such that the first major surface of the first sheet comprises a plurality of non-adhesive portions alternating with the plurality of adhesive portions, wherein each non-adhesive portion is free of the adhesive, wherein the liner assembly further comprises a plurality of indicators disposed along the plurality of lines of weakness, wherein each indicator is aligned with a corresponding non-adhesive portion from the plurality of non-adhesive portions, and wherein a maximum width of each indicator is greater than a width of each of the respective lines of weakness.

4. The warming blanket of claim 3, wherein at least two lines of weakness from the respective lines of weakness intersect each other, and wherein at least one indicator from the plurality of indicators is disposed at an intersection between the at least two lines of weakness.

5. The warming blanket of claim 1, wherein the adhesive layer comprises a plurality of adhesive portions spaced apart from each other, such that the first major surface of the first sheet comprises a plurality of non-adhesive portions alternating with the plurality of adhesive portions, and wherein each non-adhesive portion is free of the adhesive.

6. The warming blanket of claim 5, wherein:
 each adhesive portion extends along a longitudinal axis of the first major surface from a first end of the first major surface to an opposing second end of the first major surface; and
 each non-adhesive portion extends at least partially along the longitudinal axis of the first major surface.

7. The warming blanket of claim 6, wherein a length of each non-adhesive portion is at least 30% of a length of the first major surface along the longitudinal axis.

8. The warming blanket of claim 7, wherein the length of at least one of the plurality of non-adhesive portions is substantially equal to the length of the first major surface.

9. The warming blanket of claim 6, wherein the first major surface further comprises a first transverse edge and an opposing second transverse edge, each of the first transverse edge and the second transverse edge extending from the first end to the second end, and wherein the plurality of non-adhesive portions comprises a set of first non-adhesive edge portions extending along the first transverse edge and a set of second non-adhesive edge portions extending along the second transverse edge.

10. The warming blanket of claim 9, wherein:
 each first non-adhesive edge portion extends partly along the first transverse edge;
 each second non-adhesive edge portion extends partly along the second transverse edge; and
 each non-adhesive portion disposed between the set of first non-adhesive edge portions and the set of second non-adhesive edge portions extends from the first end of the first major surface to the second end of the first major surface.

11. The warming blanket of claim 9, wherein:
 the set of first non-adhesive edge portions comprises a pair of first non-adhesive edge portions spaced apart from each other with respect to the longitudinal axis of the first major surface; and
 the set of second non-adhesive edge portions comprises a pair of second non-adhesive edge portions spaced apart from each other with respect to the longitudinal axis of the first major surface.

12. The warming blanket of claim 11, wherein the first major surface comprises:
 a first surface portion extending from the first end of the first major surface and having a first width from the first transverse edge to the second transverse edge, the first surface portion comprising one of the pair of first non-adhesive edge portions and one of the pair of second non-adhesive edge portions;
 a second surface portion extending from the second end of the first major surface and having a second width from the first transverse edge to the second transverse edge, the second surface portion comprising the other of the pair of first non-adhesive edge portions and the other of the pair of second non-adhesive edge portions; and
 a third surface portion disposed between the first surface portion and the second surface portion with respect to the longitudinal axis, the third surface portion having a third width from the first transverse edge to the second transverse edge less than each of the first width and the second width, the third surface portion being at least partially covered by respective adhesive portions from the plurality of adhesive portions at the first transverse edge and the second transverse edge.

13. The warming blanket of claim 9, wherein at least one release liner from the plurality of release liners extends from the first transverse edge to the second transverse edge to at least partially cover each of the plurality of non-adhesive portions.

14. The warming blanket of claim 5, wherein the plurality of non-adhesive portions forms at most 75% of the first major surface.

15. The warming blanket of claim 5, wherein each release liner at least partially covers at least one non-adhesive portion.

16. A warming blanket for warming a patient, the warming blanket comprising:
a first sheet comprising a first major surface of the warming blanket;
a second sheet comprising a second major surface of the warming blanket opposite to the first major surface, wherein the second sheet is sealingly joined to the first sheet to form one or more inflatable portions between the first sheet and second sheet;
an adhesive layer comprising a plurality of adhesive portions disposed on the first major surface of the first sheet and spaced apart from each other, such that the first major surface of the first sheet comprises a plurality of non-adhesive portions alternating with the plurality of adhesive portions, wherein each adhesive portion comprises an adhesive, and wherein each non-adhesive portion is free of the adhesive; and
a liner assembly disposed on the adhesive layer opposite to the first major surface and fully covering the adhesive layer, the liner assembly comprising a plurality of release liners delimited from each other and releasably bonded to the adhesive layer, such that each release liner is independently removable from the liner assembly to expose a corresponding portion of the adhesive layer;
wherein each of the first sheet, the adhesive layer, and the plurality of release liners is air-permeable.

17. The warming blanket of claim 16, wherein the liner assembly further comprises a plurality of lines of weakness, and wherein adjacent release liners from the plurality of release liners are detachably joined to each other along respective lines of weakness from the plurality of lines of weakness.

18. The warming blanket of claim 16, wherein:
each adhesive portion extends along a longitudinal axis of the first major surface from a first end of the first major surface to an opposing second end of the first major surface; and
each non-adhesive portion extends at least partially along the longitudinal axis of the first major surface.

19. A method of using a warming blanket having a first sheet, a second sheet sealingly joined to the first sheet to form one or more inflatable portions between the first sheet and the second sheet, an adhesive layer disposed on at least a portion of a first major surface of the first sheet, and a liner assembly disposed on and fully covering the adhesive layer, the liner assembly having a plurality of release liners, the method comprising:
removing at least one release liner from the liner assembly to expose at least a portion of the adhesive layer;
placing the warming blanket on a patient, such that the first major surface faces the patient;
adhering the warming blanket to a surface via the portion of the adhesive layer exposed by removing the at least one release liner; and
inflating the one or more inflatable portions between the first sheet and the second sheet with warm air via an inlet, such that the warm air fluidly communicates with the patient through the first sheet, the adhesive layer, and at least one of the plurality of release liners.

20. The method of claim 19, wherein removing the at least one release liner from the liner assembly further comprises detaching the at least one release liner from the liner assembly along one or more respective lines of weakness.

* * * * *